(12) United States Patent
Vielma

(10) Patent No.: US 10,683,213 B2
(45) Date of Patent: Jun. 16, 2020

(54) WATER QUALITY DETECTION AND DIVERSION DEVICE, SYSTEM, AND METHOD

(71) Applicant: Marcos Vielma, San Jose, CA (US)

(72) Inventor: Marcos Vielma, San Jose, CA (US)

(*) Notice: Subject to any disclaimer, the term of this patent is extended or adjusted under 35 U.S.C. 154(b) by 229 days.

(21) Appl. No.: 16/004,005

(22) Filed: Jun. 8, 2018

(65) Prior Publication Data

US 2018/0354810 A1 Dec. 13, 2018

Related U.S. Application Data

(60) Provisional application No. 62/674,881, filed on May 22, 2018, provisional application No. 62/518,716, filed on Jun. 13, 2017.

(51) Int. Cl.

| | |
|---|---|
| *C02F 1/00* | (2006.01) |
| *G01N 33/18* | (2006.01) |
| *C02F 1/02* | (2006.01) |
| *C02F 1/44* | (2006.01) |
| *C02F 1/28* | (2006.01) |

(Continued)

(52) U.S. Cl.
CPC .............. *C02F 1/008* (2013.01); *B01D 39/16* (2013.01); *C02F 1/001* (2013.01); *C02F 1/02* (2013.01); *C02F 1/281* (2013.01); *C02F 1/283* (2013.01); *C02F 1/44* (2013.01); *G01N 33/1893* (2013.01); *C02F 2101/006* (2013.01); *C02F 2201/005* (2013.01); *C02F 2209/005* (2013.01); *C02F 2209/36* (2013.01); *C02F 2301/043* (2013.01); *C02F 2303/04* (2013.01); *C02F 2307/14* (2013.01)

(58) Field of Classification Search
CPC .... C02F 1/008; C02F 1/02; C02F 1/44; C02F 1/283; C02F 1/001; C02F 1/281; C02F 2209/005; C02F 2209/36; C02F 2301/043; C02F 2307/14; C02F 2201/005; C02F 2303/04; C02F 2101/006; G01N 33/1893; B01D 39/16
See application file for complete search history.

(56) References Cited

U.S. PATENT DOCUMENTS

| | | |
|---|---|---|
| 4,162,218 A | 6/1979 | McCormick |
| 5,401,421 A * | 3/1995 | Blum ..................... B01D 61/04 |
| | | 210/149 |
| 5,406,657 A | 4/1995 | Donati |

(Continued)

*Primary Examiner* — Jonathan M Dunlap

(57) ABSTRACT

A device, method, and processor-readable medium for water quality detection and diversion are disclosed. Water entering a building's plumbing system is tested for impurities before it routes for consumption. Impurities in the water could include bacteria, viruses, chemicals, toxins, fertilizers, minerals, biological weapons, radioactive materials, and radioactive waste. Sensors are located throughout the device to check for impurities in the water as it travels through the building's plumbing. Certain sensors decide how to route the water through various treatments within the device. Treatments to the impure water could include multi-level filtration and heating/cooling cycles for a prescribed time period to reduce impurities below an EPA-approved threshold. If the water still retains impurities after treatment in the device, the device can decide to divert the water out of the building to prevent consumption and illness to building occupants.

20 Claims, 3 Drawing Sheets

(51) Int. Cl.
   *B01D 39/16*    (2006.01)
   *C02F 101/00*   (2006.01)

(56) References Cited

U.S. PATENT DOCUMENTS

| | | |
|---|---|---|
| 6,702,942 B1 | 3/2004 | Nield |
| 9,616,388 B2 * | 4/2017 | Pimentel ................ B01D 61/12 |
| 10,214,880 B2 * | 2/2019 | Robb ...................... E03B 1/042 |
| 2010/0300951 A1 | 12/2010 | Vierling et al. |
| 2011/0083755 A1 | 4/2011 | Dolo Masnou |
| 2012/0199220 A1 | 8/2012 | Knepp et al. |
| 2013/0126430 A1 * | 5/2013 | Kenley .................. B01D 61/00 210/638 |
| 2013/0180928 A1 | 7/2013 | Vielma |
| 2014/0083846 A1 * | 3/2014 | Moon .................... B01D 61/12 204/274 |
| 2014/0116929 A1 | 5/2014 | Williamson |
| 2015/0321128 A1 | 11/2015 | Gross |
| 2016/0177545 A1 | 6/2016 | Robb et al. |
| 2017/0145669 A1 * | 5/2017 | Klicpera .................. E03C 1/00 |

* cited by examiner though not limiting only to such values and configurations. The diagrams depicted in the figures presented herein are provided for exemplary purposes only and are not considered limiting features of the disclosed embodiments.

WATER QUALITY DETECTION AND DIVERSION DEVICE, SYSTEM, AND METHOD

CROSS-REFERENCE TO PROVISIONAL APPLICATION

This application claims priority under 35 U.S.C. 119(e) to U.S. Provisional Patent Application Ser. No. 62/518,716, entitled "Water Quality Detection Device," which was filed on Jun. 13, 2017, the disclosure of which is incorporated herein by reference in its entirety. This application also claim priority under 35 U.S.C. 119(e) to U.S. Provisional Patent Application Ser. No. 62/674,881, entitled "WATER QUALITY DETECTION AND DIVERSION DEVICE AND SYSTEM," which was filed on May 22, 2018, the disclosure of which is incorporated herein by reference in its entirety.

TECHNICAL FIELD

Embodiments are generally related to a water quality detection device. Embodiments are additionally related to a method for detecting water impurities. Embodiments also relate to a device for preventing water impurities from entering a building's water system.

BACKGROUND

Improved water quality in commercial and residential buildings is essential to maintaining health and safety of people that occupy and utilize those spaces. When water is contaminated with chemicals, pathogens, and Bio Chemical Agents, it can significantly impact human health, with outcomes ranging from mild side effects to death. Water contamination is usually identified once humans get sick after ingesting contaminated water. Some of the most common pathogen contaminants can include *Norovirus, Hepatitis A, E. coli*, and *Legionella*.

Non-health related effects of water contamination include economic and environmental impact with significant impact to a community's infrastructure and economic growth. Municipal water suppliers often fail to appropriately test water supplies for contaminants. Current methods of water contamination detection are inefficient and inaccurate at detecting all contaminants. The recent water contamination crisis in Flint, Mich. demonstrates the need for improved water detection devices. Water tests conducted in 2015 in Flint showed a dangerously high level of lead. Flint officials failed to treat the water supply with an anti-corrosive agent, thus allowing iron water mains to erode. This erosion leached dangerous chemicals into Flint's water supply over a number of years.

Accordingly, the method, system, apparatus, and software program disclosed herein are intended to solve such problems such that water contamination is detected and diverted before consumption.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, an aspect of the disclosed embodiments to provide an improved water quality detection device.

In addition, it is aspect of the embodiments to provide a method for detecting water impurities.

It is another aspect of the disclosed embodiments to provide a device for preventing water impurities from entering a building's water system.

The aforementioned aspects and other objectives and advantages can now be achieved as described herein. Advantages include: Protecting the Nations' water supplies, upgrading current water plumbing codes from 20th century to 21st century plumbing standards to create a better way of managing our water supplies for current and future use, implementing computer technology into the construction industry, and making an immediate impact on the environment by improving our current infrastructure and take preventive steps to protect consumers. A device, system, and method for detecting water quality are disclosed. In an example embodiment, sensor detector detects an impurity in water in a plumbing system of a building. A sensor directional valve then routes the water through a first filter or to a water heating device. An output sensor routes water for consumption if the water contains an impurity at or below a threshold for impurities in the water. A sensor and shutoff valve in the device decides whether to shut off water flow if the impurity is detected and whether to send a report on the water impurity to a water utility company. A water heating component in the device heats the water with impurities to a preferred temperature range to kill impurities and then a cooling coil that cools the water. An output sensor in the device senses the water after the water is treated in a water heating device, a cooling, coil, and a second filter. The output sensor decides whether to route the water through a plumbing system for consumption if the water does not contain impurities above a threshold level. The impurity can be bacteria, viruses, chemicals, toxins, fertilizers, minerals, biological weapons, radioactive materials, and radioactive waste. The first filter and second filter of the device can be a membrane filter, a charcoal filter, a sand filter, or a polypropylene filter and the second filter comprises a membrane filter, a charcoal filter, a sand filter, or a polypropylene filter.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
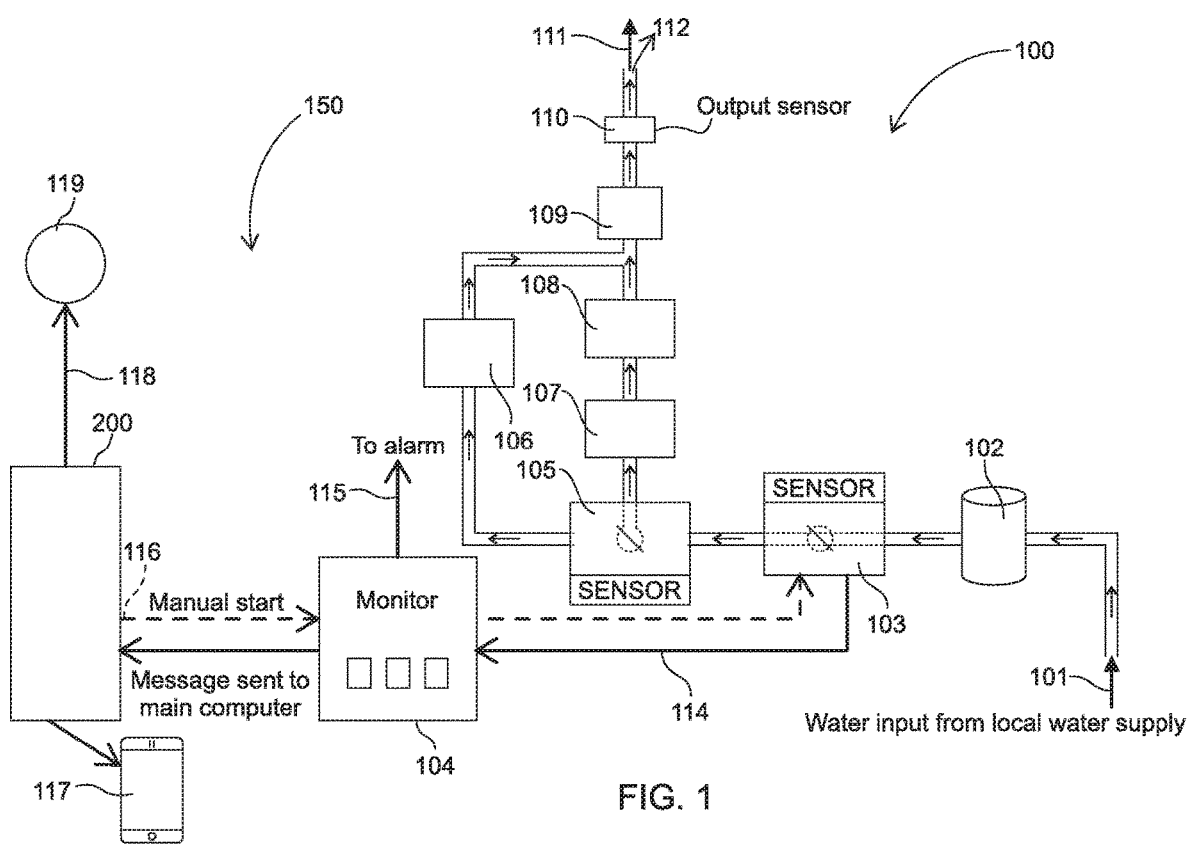
FIG. 1 illustrates a device 100 for detecting and diverting impure water, which can be implemented in accordance with an example embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be interpreted in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood, at least in part, from usage in context. For example, terms such as "and", "or", or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term one or more as used herein, depending at least in part upon context, may be used to describe any feature, structure, or characteristic in a singular sense or may be used to describe combinations of features, structures, or characteristics in a plural sense. Similarly, terms such as "a", "an", or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

A device, system, and processor-readable medium for water quality detection and diversion are disclosed. Water entering a building's plumbing system is tested for impurities before it routes for consumption. Impurities in the water could include bacteria, viruses, chemicals, toxins, fertilizers, minerals, biological weapons, radioactive materials, and radioactive waste. Sensors are located throughout the device to check for impurities in the water as it travels through the building's plumbing. Certain sensors decide how to route the water through various treatments within the device. Treatments to the impure water could include multi-level filtration and heating/cooling cycles for a prescribed time period to reduce impurities below an EPA-approved threshold. If the water still retains impurities after treatment in the device, the device can decide to divert the water out of the building to prevent consumption and illness to building occupants. The disclosed device can be installed in various locations in a building such as, for example: front of the building near water utilities, in a crawl space below the building, within interior building walls, within exterior building walls, and in an attic or basement.

In FIG. 1, a device 100 for detecting and diverting impure water is disclosed. The disclosed embodiments describe a device 100 for detecting impurities in water and diverting impure water out of a building's plumbing. The device 100 easily integrates into a system when installed with a building's existing plumbing system. A building can include a home, apartment building, office building, warehouse, etc. Impurities may include the following either alone or in combination: bacteria, viruses, chemicals, toxins, fertilizers, minerals, biological weapons, radioactive materials, radioactive waste, etc. Potable water flows from a water source through a building's plumbing 101. Several sensors throughout the device detect impurities in the water flowing in a building's plumping 101.

The sensor detector 102 detects water impurities from the water source. If the sensor detector 102 detects pure water over an acceptable EPA threshold, the sensor and shut off valve 103, while in communication with water utilities via the data processing system 200 in FIGS. 2-3, allows the water to continue flowing in the pipes of the building's water system.

If the sensor detector 102 detects impurities in the water under an acceptable threshold, while in communication with data processing device 200, the sensor and shut off valve 103 does not allow the water to continue flowing in the pipes of the building's water system. If the water shuts off after impurities are detected, the sensor and shut off valve 103 sends a message to the computer panel 104 in data processing device 200, as disclosed in FIGS. 2-3. The computer panel 104 then sends an alarm message 115 via WiFi to the building occupant, water utilities employee, or mobile communication device user informing of the water shutoff from detected water impurities. Building occupant, water utilities employee, or mobile communication device user can also be informed on computer panel 104 of type of impurity, or impurities, detected, severity of impurity below an EPA threshold, and/or proposed solutions to fix the detected impurity. The device 100 waits for instant feedback from the water utility to direct appropriate purification methods. A water utility employee monitors contaminants in the water flowing through device 100.

If water continues to flow through the pipes after passing through the sensor and shut off valve 103, then it passes through a sensor directional valve 105. The sensor directional valve 105 determines whether to send the water though a first filter 106 or through a water heating device 107. The water heating device 107 heats the water to kill bacteria and other impurities. If the water goes through a first filter 106, it then passes through a second filter 109. For example, the first filter 106 and second filter 109 can comprise the following filter types: Membrane, Charcoal, Sand, and Polypropylene. First filter 106 and second filter 109 can comprise the same type of filters or different filters.

If the sensor directional valve 105 determines not to filter the water though the first filter 106, then the water passes through a water heating device 107. If the sensor directional valve 105 detects bacteria and/or viruses in the water, it decides to send the water through the water heating device 107 instead of the first filter 106 which may not remove all bacterial and viral impurities. The water heating device 107 will purify the water by killing certain types of impurities, including bacteria and viruses. The water heating device heats the water in the pipes to a preferable temperature range of 160° Fahrenheit to 212° Fahrenheit for no more than five minutes depending on the type of impurity present in the water. The water in the pipes then passes through a cooling coil 108 to cool to a temperature of 60° Fahrenheit. The water cools as it passes through the cooling coil 108. The device may not filter the water in the pipes through the water heating device 107 because the water may be above an appropriate threshold for impurities.

Water exits the cooling coil 108 and enters the second filter 109. The water exits the second filter and passes through an output sensor 110. Output sensor 110 determines whether the water is free of impurities by comparing the water composition to Environmental Protection Agency (EPA) purity thresholds. If the water is pure, then the water passes into the building's faucets 111 for consumption. If the output sensor 110 determines the water still contains impurities, then the device 100 drains the water out of the building 112 rather than sending it through faucets for consumption. If the impure water is consumed by building occupants or device user, it could cause illness or death.

Computer panel 104 monitors the device via the shutoff valve 103. Computer panel 104 may comprise a novel piece of hardware with a graphical user interface, or an existing computer system as a data processing device 200, as described in FIGS. 2-3 herein. The novel hardware can comprise a computer/mobile system, fully-described in FIGS. 2-3, installed into wall of the building to monitor water purification levels in the device 100. Computer panel 104 integrates with an alarm 111 to alert the building occupants of impurities in the water. Computer panel 104 integrates with the data processing system 200 to send automatic or manual messages 118 to an entity 119, about the detected water impurities. The entity 119 can comprise: to a water company, the Department of Homeland Security, another person, a security company, and/or software application viewed on a smartphone and/or tablet 117. Building occupant or device user can manually start 116 the device 100 from the data-processing system 200, as described in FIGS. 2-3.

Figure 2:
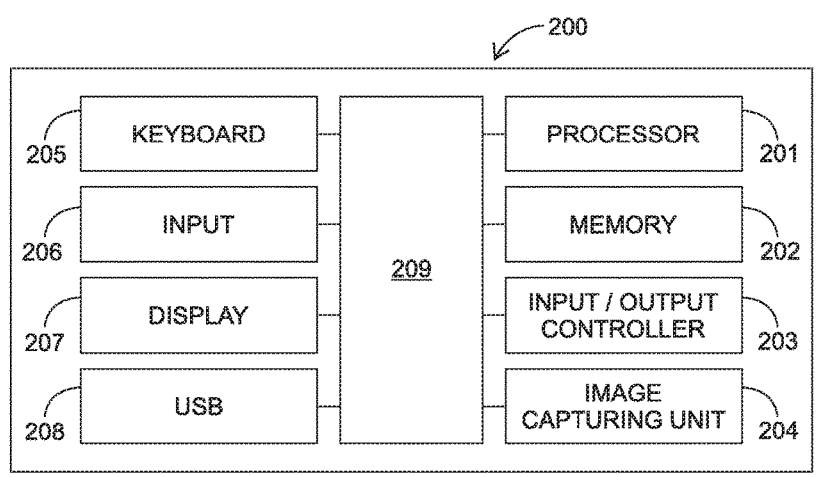
FIG. 2 illustrates a schematic view of a software system 200 including a module, an operating system, and a user interface, in accordance with an example embodiment.
Figure 3:
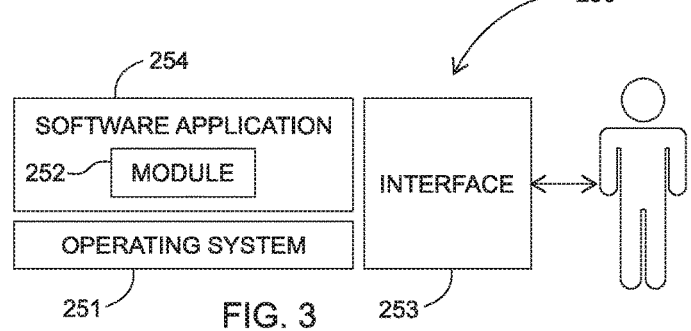
FIG. 3 illustrates a system 250 for detecting and diverting impure water, which can be implemented in accordance with an example embodiment.

FIGS. 2-3 are provided as exemplary diagrams of data-processing environments in which embodiments may be implemented. It should be appreciated that FIGS. 2-3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 2, some embodiments may be implemented in the context of a data-processing system 200 that can include one or more processors such as processor 201, a memory 202, a controller 203 (e.g., an input/output controller), a peripheral USB (Universal Serial Bus) connection 208, a keyboard 205 (e.g., a physical keyboard or a touch screen graphically displayed keyboard), an input component 206 (e.g., a pointing device, such as a mouse, track ball, pen device, which may be utilized in association or with the keyboard 205, etc.), a display 207, and in some cases, an image-capturing unit 204 (e.g., a digital video camera, an ALPR camera, etc.). Data-processing system 200 may be, for example, a client computing device (e.g., a client PC, laptop, tablet computing device, etc.), which communicates with peripheral devices (not shown) via a client-server network (e.g., wireless and/or wired). In another embodiment, the data-processing system may be a server in the context of a client-server network or other server-based network implementation.

As illustrated, the various components of data-processing system 200 can communicate electronically through a system bus 209 or other similar architecture. The system bus 209 may be, for example, a subsystem that transfers data between, for example, computer components within data-processing system 200 or to and from other data-processing devices, components, computers, etc. Data-processing system 200 may be implemented as, for example, a server in a client-server based network (e.g., the Internet) or can be implemented in the context of a client and a server (i.e., where aspects are practiced on the client and the server). Data-processing system 200 may be, for example, a stand-alone desktop computer, a laptop computer, a Smartphone, a pad computing device, a server, and so on.

FIG. 3 illustrates a computer software system 250 for directing the operation of the data-processing system 200 shown in FIG. 2. Software application 254, stored for example in memory 202, generally includes a kernel or operating system 251 and a shell or interface 253. One or more application programs, such as software application 254, may be "loaded" (i.e., transferred from, for example, memory 202 or another memory location) for execution by the data-processing system 200. The data-processing system 200 can receive user commands and data through the interface 253; these inputs may then be acted upon by the data-processing system 200 in accordance with instructions from operating system 251 and/or software application 254. The interface 253, in some embodiments, can serve to display results, whereupon a user may supply additional inputs or terminate a session.

The software application 254 can include one or more modules such as, for example, a module 252 (or a module composed of a group of modules), which can, for example, implement instructions or operations such as those described herein. Examples of instructions that can be implemented by module 252 include steps or operations such as those shown and described herein with respect to the various blocks and operations shown in FIG. 1 and described elsewhere herein. Module 252 can include sub-modules such as, for example, the various modules shown in FIG. 4.

The following discussion is intended to provide a brief, general description of suitable computing environments in which the system and method may be implemented. Although not required, the disclosed embodiments will be described in the general context of computer-executable instructions, such as program modules, being executed by a single computer. In most instances, a "module" such as module 252 shown in FIG. 3 constitutes a software application. However, a module may also be composed of, for example, electronic and/or computer hardware or such hardware in combination with software. In some cases, a "module" can also constitute a database and/or electronic hardware and software that interact with such a database. For example, sensor directional value module 305 shown in FIG. 5 may include or direct the operations of the sensor directional valve 105 depicted in FIG. 1.

Generally, program modules include, but are not limited to, routines, subroutines, software, applications, programs, objects, components, data structures, etc., that perform particular tasks or implement particular abstract data types and instructions. Moreover, those skilled in the art will appreciate that the disclosed method and system may be practiced with other computer system configurations, such as, for example, hand-held devices, multi-processor systems, data networks, microprocessor-based or programmable consumer electronics, networked PCs, minicomputers, mainframe computers, servers, and the like.

Note that the term module as utilized herein can refer to a collection of routines and data structures that perform a particular task or implement a particular abstract data type. Modules may be composed of two parts: an interface, which lists the constants, data types, variable, and routines that can be accessed by other modules or routines; and an implementation, which is typically private (accessible only to that module) and which includes source code that actually implements the routines in the module. The term module may also simply refer to an application, such as a computer program designed to assist in the performance of a specific task, such as word processing, accounting, inventory management, etc. Thus, the instructions or steps such as those shown in FIG. 1, for example, and discussed elsewhere herein can be implemented in the context of such a module or modules, sub-modules, and so on. Examples of such modules are also shown in FIG. 4.

FIGS. 2-3 are thus intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including, for example, Windows, Macintosh, UNIX, LINUX, and the like.

Figure 4:
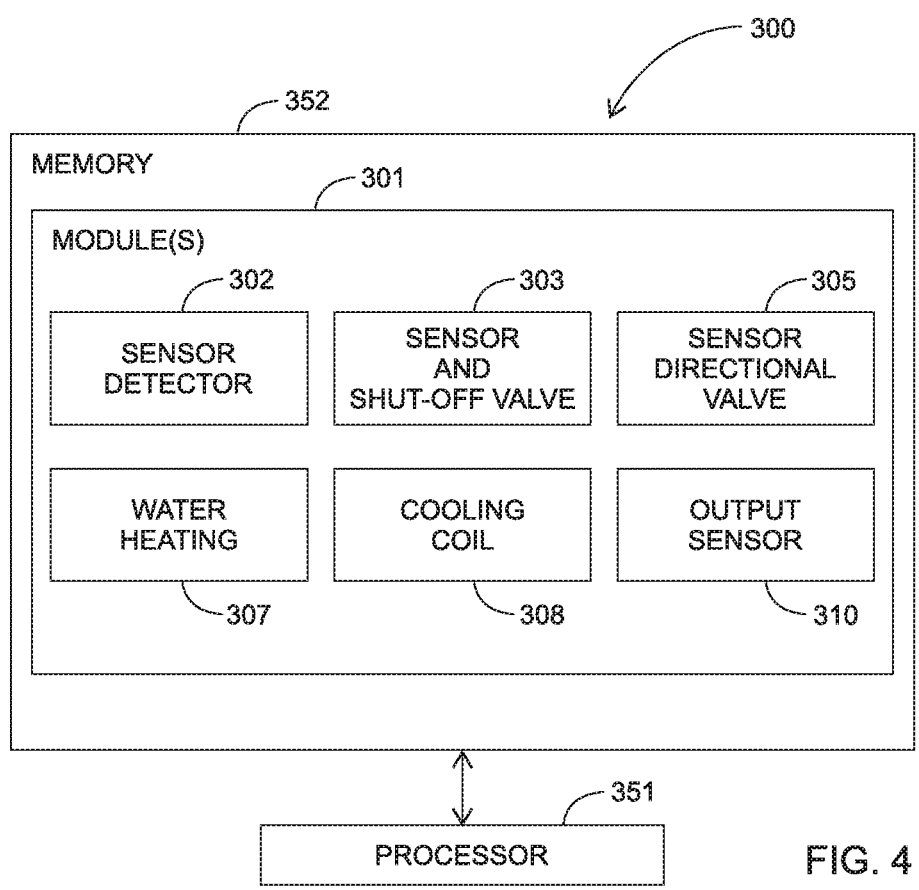
FIG. 4 illustrates a block diagram of computer-implemented modules 300 for the detection and diversion of water containing impurities, in accordance with an example embodiment.

FIG. 4 illustrates a block diagram of computer-implemented modules in a system 300 for the detection and diversion of water containing impurities, in accordance with an example embodiment. The system 300 shown in FIG. 4 includes a memory 352 that communicates bidirectionally and electronically with a processor 351. The memory 352 stores a module 301 (or a group of modules) composed of, for example, a sensor detector module 302, a sensor and shutoff valve module 303, a sensor directional valve module 305, a water heating module 307, a cooling coil module 308, and an output sensor module 310.

Note that such modules include instructions that implement the various operational steps discussed herein with respect to the device and system shown in FIG. 1. For example, the sensor detector module 302 depicted in FIG. 4 implements the instructions associated with the sensor detector block 102 shown in FIG. 1; the sensor and shutoff valve module 303 depicted in FIG. 4 implements the instructions associated with the sensor and shutoff valve block 103 in FIG. 1; the sensor directional valve module 305 depicted in FIG. 4 implements the instructions associated with the sensor directional valve block 105 in FIG. 1, the water heating module 307 depicted in FIG. 4 implements the instructions associated with the water heating device block 107 in FIG. 1; the cooling coil module 308 depicted in FIG. 4 implements the instructions associated with the cooling coil block 108 depicted in FIG. 1, and the output sensor module 310 depicted in FIG. 4 implements the instructions associated with the output sensor block 110 depicted in FIG. 1.

The sensor detector module 302 thus includes instructions for sensing water entering a building's plumbing system for impurities. The sensor and shut off valve module 303 includes instructions for passing the water through to the sensor directional valve 105 for purification through the device. The sensor directional valve module 305 includes instructions for sending water through a first filter 106 or a water heating device 107 based on an acceptable threshold amount of impurities in the water. Automatic updates of thresholds can also be programmed into sensor and shutoff module 303, sensor directional valve module 305, or manually entered by a user of the device 100. The water heating module 307 includes instructions for heating the water to a preferred temperature range from 160° Fahrenheit to 212° Fahrenheit for a certain time period. The cooling coil module 308 contains instructions for cooling the water to a particular temperature after it passed through the water heating device 107. The output sensor module 310 contains instructions for allowing the purified water to flow through the faucets in the building 111 for consumption or to divert the water out of the building 112 if it still contains impurities.

Note that in some embodiments, computer program code for carrying out operations of the disclosed embodiments may be written in an object oriented programming language (e.g., Java, C #, C++, etc.). Such computer program code, however, for carrying out operations of particular embodiments can also be written in conventional procedural programming languages, such as the "C" programming language or in a visually oriented programming environment, such as, for example, Visual Basic.

The program code may execute entirely on the user's computer, partly on the user's computer, as a stand-alone software package, partly on the user's computer and partly on a remote computer, or entirely on the remote computer. In the latter scenario, the remote computer may be connected to a user's computer through a local area network (LAN) or a wide area network (WAN), wireless data network e.g., Wimax, IEEE 802.xx, and cellular network, or the connection may be made to an external computer via most third party supported networks (e.g., through the Internet via an Internet Service Provider).

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the various block or blocks, flowcharts, and other architecture illustrated and described herein.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Based on the foregoing, it can be appreciated that a number of embodiments, preferred and alternative, are disclosed herein. The techniques/embodiments described herein are in no way meant to limit the breadth of potential applications. For example, in one embodiment a device for detecting water quality is disclosed. The device comprise: a sensor detector that detects an impurity in water, wherein the water is in a plumbing system of a building; a sensor directional valve associated with the sensor detector, wherein the sensor directional valve routes the water through a first filter or to a water heating device; and an output sensor associated with the sensor detector and the sensor directional valve, wherein the output sensor routes water for consumption if the water contains an impurity at or below a threshold for impurities in the water. In another embodiment, the device includes a sensor and shutoff valve that shuts off water flow if the impurity is detected, wherein the impurity is present in a quantity above a threshold; wherein the sensor and shutoff valve sends a signal to a computer panel; wherein the computer panel is integrated into a data-processing system; and wherein a water utility company directs a user of the device to let impure water flow through the device for treatment.

In an alternate embodiment, the device further comprises a water heating device that heats the water with impurities to a preferred temperature range of 160 degrees Fahrenheit to 212 degrees Fahrenheit in a range of one to five minutes, wherein the water is heated for an appropriate amount of time to kill impurities in the water; and a cooling coil that cools the water after the water passes through the heating device; wherein the water is cooled for an appropriate amount of time as the water passes through the cooling coil to a preferred temperate range of 60 degrees Fahrenheit.

In yet another embodiment, the device further comprises an output sensor that senses the water after the water is treated in a water heating device, a cooling, coil, and a second filter; wherein the output sensor determines to route the water through a plumbing system for consumption if the water does not contain impurities above a threshold level. In an embodiment, the device further comprises an output sensor that senses the water after the water is treated in a water heating device, a cooling, coil, and a second filter; wherein the output sensor diverts the water out of the plumbing system if the water contains impurities above a threshold level after the water passes through the heating device, cooling coil, and a second filter.

In some example embodiments, the impurity comprises bacteria, viruses, chemicals, toxins, fertilizers, minerals, biological weapons, radioactive materials, and radioactive waste. In yet another example embodiment, the first filter comprises a membrane filter, a charcoal filter, a sand filter, or a polypropylene filter and the second filter comprises a membrane filter, a charcoal filter, a sand filter, or a polypropylene filter.

In another embodiment, a method for detecting water quality is disclosed. Such a method may include the steps of: detecting an impurity in water in a device via a sensor detector, wherein the water is in a plumbing system of a building; routing the water through a first filter or to a water heating device via a sensor directional valve, wherein the sensor directional valve is associated with the sensor detector; and routing the water for consumption via an output sensor if the water contains an impurity at or below a threshold for impurities in the water, wherein the output sensor associated with the sensor detector and the sensor directional valve. The method may also include the steps of: shutting off a flow of the water via a sensor and shutoff valve if an impurity is detected, wherein said impurity is present in a quantity above a threshold; sending a signal to a computer panel via the sensor and shutoff valve wherein the computer panel is integrated into a data-processing system; and receiving an instruction from a water utility company to let impure water flow through the device for treatment.

In yet another embodiment, the method may include the steps of: heating the water with impurities via a water heating device to a preferred temperature range of 160° Fahrenheit to 212° Fahrenheit, wherein the water is heated for an appropriate amount of time to kill impurities in the water and cooling the water via a cooling coil after the water passes through the heating device; wherein the water is cooled for an appropriate amount of time as the water passes through the cooling coil to a preferred temperate range of 60 degrees Fahrenheit.

In an embodiment, the method can further comprise the steps of: sensing the water via an output sensor after the water is treated in a water heating device, a cooling, coil, and a second filter; and determining via the output sensor to route the water through a plumbing system for consumption if the water does not contain impurities above a threshold level. In another embodiment, the method can further comprise the steps of: sensing the water via an output sensor after the water is treated in a water heating device, a cooling, coil, and a second filter; and diverting the water via the output sensor out of the plumbing system if the water contains impurities above a threshold level after the water passes through the heating device, cooling coil, and a second filter. In another example embodiment, the first filter comprises a membrane filter, a charcoal filter, a sand filter, or a polypropylene filter; the second filter comprises a membrane filter, a charcoal filter, a sand filter, or a polypropylene filter; and the impurity comprises bacteria, viruses, chemicals, toxins, fertilizers, minerals, biological weapons, radioactive materials, and radioactive waste.

In an embodiment, a non-transitory processor-readable medium storing computer code representing instructions to cause a process for detecting impure water is disclosed. For example, the instructions comprise code to detect an impurity in water via a sensor detector, wherein the water is in a plumbing system of a building; route the water through a first filter or to a water heating device via a sensor directional valve, wherein the sensor directional valve is associated with the sensor detector; and route the water for consumption via an output sensor if the water contains an impurity at or below a threshold for impurities in the water, wherein the output sensor associated with the sensor detector and the sensor directional valve. In another embodiment, the instructions comprise code to shut off a flow of the water via a sensor and shutoff valve if an impurity is detected, wherein said impurity is present in a quantity above a threshold; send a signal to a computer panel via the sensor and shutoff valve wherein the computer panel is integrated into a data-processing system; and receive an instruction from a water utility company to let impure water flow through the device for treatment.

In yet another embodiment, the instructions comprise code to heat the water with impurities via a water heating device to a preferred temperature range of 160° Fahrenheit to 212° Fahrenheit, wherein the water is heated for an appropriate amount of time to kill impurities in the water; and cool the water via a cooling coil after the water passes through the heating device; wherein the water is cooled for an appropriate amount of time as the water passes through the cooling coil to a preferred temperate range of 60 degrees Fahrenheit. In an embodiment, the instructions comprise code to sense the water via an output sensor after the water is treated in a water heating device, a cooling, coil, and a second filter; determine via the output sensor to route the water through a plumbing system for consumption if the water does not contain impurities above a threshold level;

In an example embodiment, the instructions comprise code to sense the water via an output sensor after the water is treated in a water heating device, a cooling, coil, and a second filter; divert the water via the output sensor out of the plumbing system if the water contains impurities above a threshold level after the water passes through the heating device, cooling coil, and a second filter, wherein the first filter comprises a membrane filter, a charcoal filter, a sand filter, or a polypropylene filter, the second filter comprises a membrane filter, a charcoal filter, a sand filter, or a polypropylene filter, and the impurity comprises bacteria, viruses, chemicals, toxins, fertilizers, minerals, biological weapons, radioactive materials, and radioactive waste.

It will be appreciated that variations of the above-disclosed and other features and functions, or alternatives thereof, may be desirably combined into many other different systems or applications. Also, it can be appreciated that various presently unforeseen or unanticipated alternatives, modifications, variations or improvements therein may be subsequently made by those skilled in the art which are also intended to be encompassed by the following claims.

What is claimed is:

1. A device for detecting water quality, the device comprising:
    a sensor detector that detects an impurity in water, wherein the water is in a plumbing system of a building;
    a sensor directional valve associated with the sensor detector, wherein the sensor directional valve routes the water through a first filter or to a water heating device; and
    an output sensor associated with the sensor detector and the sensor directional valve, wherein the output sensor routes water for consumption if the water contains an impurity at or below a threshold for impurities in the water.

2. The device of claim 1 further comprising:
    a sensor and shutoff valve that shuts off water flow if the impurity is detected, wherein the impurity is present in a quantity above a threshold;
    wherein the sensor and shutoff valve sends a signal to a computer panel;
    wherein the computer panel is integrated into a data-processing system;
    wherein a water utility company directs a user of the device to let impure water flow through the device for treatment.

3. The device of claim 1 further comprising:
    a water heating device that heats the water with impurities to a preferred temperature range of 160 degrees Fahrenheit to 212 degrees Fahrenheit in a range of one to five minutes, wherein the water is heated for an appropriate amount of time to kill impurities in the water; and
    a cooling coil that cools the water after the water passes through the heating device; wherein the water is cooled for an appropriate amount of time as the water passes through the cooling coil to a preferred temperate range of 60 degrees Fahrenheit.

4. The device of claim 1 further comprising:
    an output sensor that senses the water after the water is treated in a water heating device, a cooling, coil, and a second filter;
    wherein the output sensor determines to route the water through a plumbing system for consumption if the water does not contain impurities above a threshold level.

5. The device of claim 1 further comprising:
    an output sensor that senses the water after the water is treated in a water heating device, a cooling, coil, and a second filter;
    wherein the output sensor diverts the water out of the plumbing system if the water contains impurities above a threshold level after the water passes through the heating device, cooling coil, and a second filter.

6. The device of claim 1 wherein the impurity comprises bacteria, viruses, chemicals, toxins, fertilizers, minerals, biological weapons, radioactive materials, and radioactive waste.

7. The device of claim 1:
    wherein the first filter comprises a membrane filter, a charcoal filter, a sand filter, or a polypropylene filter;
    wherein a second filter comprises a membrane filter, a charcoal filter, a sand filter, or a polypropylene filter.

8. A method for detecting water quality, the method comprising:
    detecting an impurity in water in a device via a sensor detector, wherein the water is in a plumbing system of a building;
    routing the water through a first filter or to a water heating device via a sensor directional valve, wherein the sensor directional valve is associated with the sensor detector; and
    routing the water for consumption via an output sensor if the water contains an impurity at or below a threshold for impurities in the water, wherein the output sensor associated with the sensor detector and the sensor directional valve.

9. The method of claim 8 further comprising:
    shutting off a flow of the water via a sensor and shutoff valve if an impurity is detected, wherein said impurity is present in a quantity above a threshold;
    sending a signal to a computer panel via the sensor and shutoff valve wherein the computer panel is integrated into a data-processing system;
    receiving an instruction from a water utility company to let impure water flow through the device for treatment.

10. The method of claim 8 further comprising:
    heating the water with impurities via a water heating device to a preferred temperature range of 160° Fahrenheit to 212° Fahrenheit, wherein the water is heated for an appropriate amount of time to kill impurities in the water; and
    cooling the water via a cooling coil after the water passes through the heating device; wherein the water is cooled for an appropriate amount of time as the water passes through the cooling coil to a preferred temperate range of 60 degrees Fahrenheit.

11. The method of claim 8 further comprising:
    sensing the water via an output sensor after the water is treated in a water heating device, a cooling, coil, and a second filter;
    determining via the output sensor to route the water through a plumbing system for consumption if the water does not contain impurities above a threshold level.

12. The method of claim 8 further comprising:
    sensing the water via an output sensor after the water is treated in a water heating device, a cooling, coil, and a second filter;
    diverting the water via the output sensor out of the plumbing system if the water contains impurities above a threshold level after the water passes through the heating device, cooling coil, and a second filter.

13. The method of claim 8 wherein:
the first filter comprises a membrane filter, a charcoal filter, a sand filter, or a polypropylene filter;
the second filter comprises a membrane filter, a charcoal filter, a sand filter, or a polypropylene filter;
the impurity comprises bacteria, viruses, chemicals, toxins, fertilizers, minerals, biological weapons, radioactive materials, and radioactive waste.

14. A non-transitory processor-readable medium storing computer code representing instructions to cause a process for detecting impure water, said computer code comprising code to:
detect an impurity in water via a sensor detector, wherein the water is in a plumbing system of a building;
route the water through a first filter or to a water heating device via a sensor directional valve, wherein the sensor directional valve is associated with the sensor detector; and
route the water for consumption via an output sensor if the water contains an impurity at or below a threshold for impurities in the water, wherein the output sensor associated with the sensor detector and the sensor directional valve.

15. The processor-readable medium of claim 14 further comprising code to:
shut off a flow of the water via a sensor and shutoff valve if an impurity is detected, wherein said impurity is present in a quantity above a threshold;
send a signal to a computer panel via the sensor and shutoff valve wherein the computer panel is integrated into a data-processing system;
receive an instruction from a water utility company to let impure water flow through the device for treatment.

16. The processor-readable medium of claim 14 further comprising code to:
heat the water with impurities via a water heating device to a preferred temperature range of 160° Fahrenheit to 212° Fahrenheit, wherein the water is heated for an appropriate amount of time to kill impurities in the water; and
cool the water via a cooling coil after the water passes through the heating device; wherein the water is cooled for an appropriate amount of time as the water passes through the cooling coil to a preferred temperate range of 60 degrees Fahrenheit.

17. The processor-readable medium of claim 14 further comprising code to:
sense the water via an output sensor after the water is treated in a water heating device, a cooling, coil, and a second filter;
determine via the output sensor to route the water through a plumbing system for consumption if the water does not contain impurities above a threshold level.

18. The processor-readable medium of claim 14 further comprising code to:
sense the water via an output sensor after the water is treated in a water heating device, a cooling, coil, and a second filter;
divert the water via the output sensor out of the plumbing system if the water contains impurities above a threshold level after the water passes through the heating device, cooling coil, and a second filter.

19. The processor-readable medium of claim 14 wherein:
the first filter comprises a membrane filter, a charcoal filter, a sand filter, or a polypropylene filter;
the second filter comprises a membrane filter, a charcoal filter, a sand filter, or a polypropylene filter.

20. The processor-readable medium of claim 14 wherein:
the impurity comprises bacteria, viruses, chemicals, toxins, fertilizers, minerals, biological weapons, radioactive materials, and radioactive waste.

* * * * *